United States Patent
Nanasawa et al.

(10) Patent No.: US 10,786,393 B2
(45) Date of Patent: Sep. 29, 2020

(54) APPARATUS FOR BODILY SENSATION OF BONE VIBRATION

(71) Applicant: NETEN INC., Kofu-shi, Yamanashi (JP)

(72) Inventors: Kenji Nanasawa, Kofu (JP); Tomoki Nanasawa, Kofu (JP); Rei Hatano, Kofu (JP)

(73) Assignee: NETEN INC., Kofu-Shi (JP)

(*) Notice: Subject to any disclaimer, the term of this patent is extended or adjusted under 35 U.S.C. 154(b) by 0 days.

(21) Appl. No.: 16/559,350

(22) Filed: Sep. 3, 2019

(65) Prior Publication Data
US 2020/0078220 A1 Mar. 12, 2020

(30) Foreign Application Priority Data
Sep. 6, 2018 (JP) .................. 2018-167107

(51) Int. Cl.
*H04R 25/00* (2006.01)
*A61F 11/04* (2006.01)
*B06B 1/02* (2006.01)
*H04R 3/00* (2006.01)

(52) U.S. Cl.
CPC ............ *A61F 11/045* (2013.01); *A61F 11/04* (2013.01); *B06B 1/0215* (2013.01); *H04R 3/00* (2013.01); *B06B 2201/76* (2013.01)

(58) Field of Classification Search
CPC .. H04R 1/025; H04R 2460/13; A61H 23/026; A61H 2201/049; A61H 2201/0165; A61H 2201/0169
See application file for complete search history.

(56) References Cited

U.S. PATENT DOCUMENTS 3,134,861 A * 5/1964 Dempsey ............... H04R 1/105
  381/326
4,064,376 A * 12/1977 Yamada ................. A47C 7/727
  381/152
(Continued)

FOREIGN PATENT DOCUMENTS

JP   S61-189689 A   8/1986
JP   H06-58748 U    8/1994
(Continued)

*Primary Examiner* — Fan S Tsang
*Assistant Examiner* — Ryan Robinson
(74) *Attorney, Agent, or Firm* — Maschoff Brennan

(57) ABSTRACT

Provided is an apparatus for bodily sensation of bone vibration. The apparatus includes: an electric signal generator configured to generate an electric signal; an amplifier configured to amplify the electric signal from the electric signal generator; a vibrator configured to transduce the amplified electric signal transmitted from the amplifier into a mechanical vibration; a metal vibration member directly coupled to a vibration generator of the vibrator, the vibration member having a seat portion configured to contact with a human body and a side surface portion continuing with the seat portion; and a seat support member provided on a back surface of the seat portion, covering the vibrator, and configured to be placed on a placement plane and to support the seat portion above and apart from the placement plane so as to keep vibrational energy from being conducted to the placement plane.

11 Claims, 13 Drawing Sheets

(56) References Cited

U.S. PATENT DOCUMENTS

| | | | | |
|---|---|---|---|---|
| 4,354,067 A * | 10/1982 | Yamada | ............. | A61H 23/0236 381/301 |
| 4,550,428 A * | 10/1985 | Yanagishima | ........... | H04R 9/04 381/407 |
| 4,641,345 A * | 2/1987 | Takahashi | .......... | A61H 23/0236 381/86 |
| 4,967,871 A * | 11/1990 | Komatsubara | ..... | A61H 23/0236 181/141 |
| 5,050,587 A * | 9/1991 | Sagara | ..................... | H02N 2/14 601/2 |
| 5,553,148 A * | 9/1996 | Werle | ..................... | H04R 5/023 381/151 |
| 6,369,312 B1 | 4/2002 | Komatsu | | |
| 6,537,234 B1 * | 3/2003 | Komatsu | ............ | A61H 23/0236 381/396 |
| 6,839,443 B2 * | 1/2005 | Fukuda | .................. | H04R 13/00 381/151 |
| 6,903,474 B2 * | 6/2005 | An | ......................... | H04R 9/066 310/15 |
| 8,027,491 B2 * | 9/2011 | Ledonne | ............. | A61H 23/0236 381/151 |
| 8,308,558 B2 * | 11/2012 | Thorner | .................. | G06F 3/011 463/30 |
| 8,638,966 B2 * | 1/2014 | Taylor | ................. | G10H 1/0008 381/333 |
| 8,668,045 B2 * | 3/2014 | Cohen | ..................... | H04R 5/04 181/150 |
| 9,143,848 B2 * | 9/2015 | Hebenstreit | .......... | G02B 27/017 |
| 9,532,123 B2 * | 12/2016 | Fukuda | ................... | H04M 1/03 |
| 9,621,973 B2 * | 4/2017 | Stauber | .................. | G10K 11/02 |
| 10,390,156 B2 * | 8/2019 | Khwaja | .................... | G08B 6/00 |
| 10,469,935 B2 * | 11/2019 | Kunimoto | .............. | H04R 1/1075 |
| 2005/0015027 A1 * | 1/2005 | Kojima | ............. | A61H 23/0236 601/57 |
| 2007/0053530 A1 * | 3/2007 | Ochiai | ................... | H04R 5/023 381/151 |
| 2011/0251535 A1 * | 10/2011 | Bender | ................. | A61M 21/02 601/49 |
| 2014/0274229 A1 * | 9/2014 | Fukuda | ................. | H04R 1/025 455/575.1 |
| 2015/0319526 A1 * | 11/2015 | Kunimoto | .............. | H04R 11/02 381/74 |
| 2020/0228904 A1 * | 7/2020 | Liao | ....................... | H04R 9/066 |

FOREIGN PATENT DOCUMENTS

| | | | | |
|---|---|---|---|---|
| JP | H7-245793 A | | 9/1995 | |
| JP | 3341238 B2 | | 8/2002 | |
| JP | 2002-346476 A | | 12/2002 | |
| JP | 2005-223630 A | | 8/2005 | |
| JP | 2005223630 A | * | 8/2005 | ............ H04R 1/025 |
| JP | 2010-011202 A | | 1/2010 | |
| JP | 2011-160869 A | | 8/2011 | |

* cited by examiner

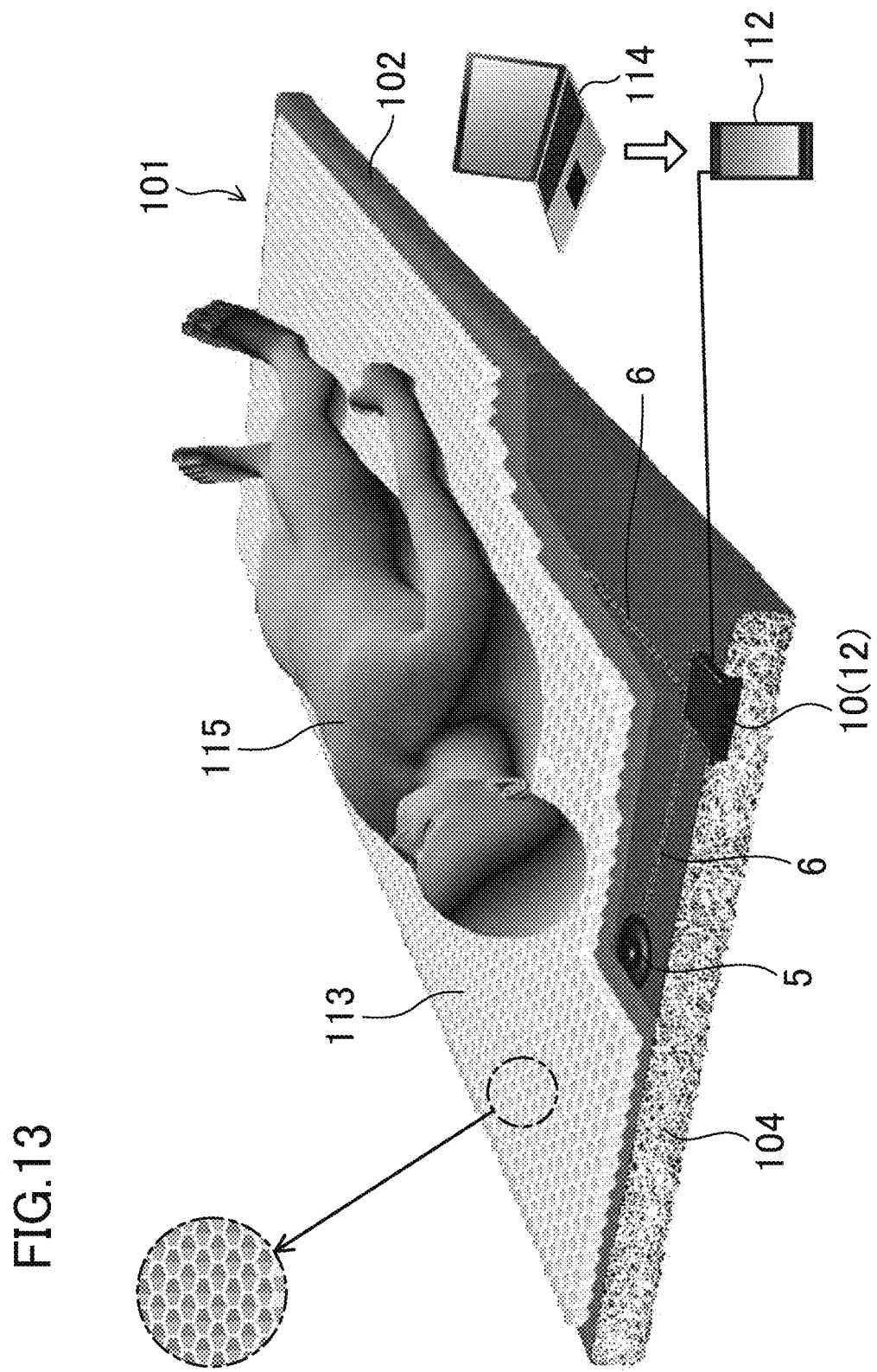

APPARATUS FOR BODILY SENSATION OF BONE VIBRATION

CROSS-REFERENCE TO RELATED APPLICATION

This application claims priority to Japanese Patent Application No. 2018-167107 filed on Sep. 6, 2018, the entire disclosure of which is incorporated by reference herein.

BACKGROUND

A speaker system has been known which includes a speaker and an electro-mechanical vibration transducer for transducing an electroacoustic signal into a mechanical vibration. A simplified wearable apparatus for bodily sensation of vibration has also been known. This apparatus includes: a bag configured to closely contact with a body; an electro-mechanical vibration transducer generating a vibration substantially conforming to the waveform of an audio signal obtained through electrically transducing an audible sound, the electro-mechanical vibration transducer being incorporated in the bag such that a vibrating surface of the electro-mechanical vibration transducer extends along a bag surface facing the body; an audio signal input terminal provided for the electro-mechanical vibration transducer; and a belt attached to the bag and configured to bring the bag in substantially close contact with the body when the bag is worn.

SUMMARY

An apparatus for bodily sensation of bone vibration includes: an electric signal generator configured to generate an electric signal; an amplifier configured to amplify the electric signal from the electric signal generator; a vibrator configured to transduce the amplified electric signal transmitted from the amplifier into a mechanical vibration; a metal vibration member directly coupled to a vibration generator of the vibrator, the vibration member having a seat portion configured to contact with a human body and a side surface portion continuing with the seat portion; and a seat support member provided on a back surface of the seat portion, covering the vibrator, and configured to be placed on a placement plane and to support the seat portion above and apart from the placement plane so as to keep vibrational energy from being conducted to the placement plane. The apparatus is configured to conduct the vibration via a part of the human body, the part being in contact with the seat portion.

BRIEF DESCRIPTION OF THE DRAWINGS

FIG. 13 is a perspective view illustrating an overall configuration of the apparatus for bodily sensation of bone vibration according to the second embodiment.

DETAILED DESCRIPTION

Figure 1:
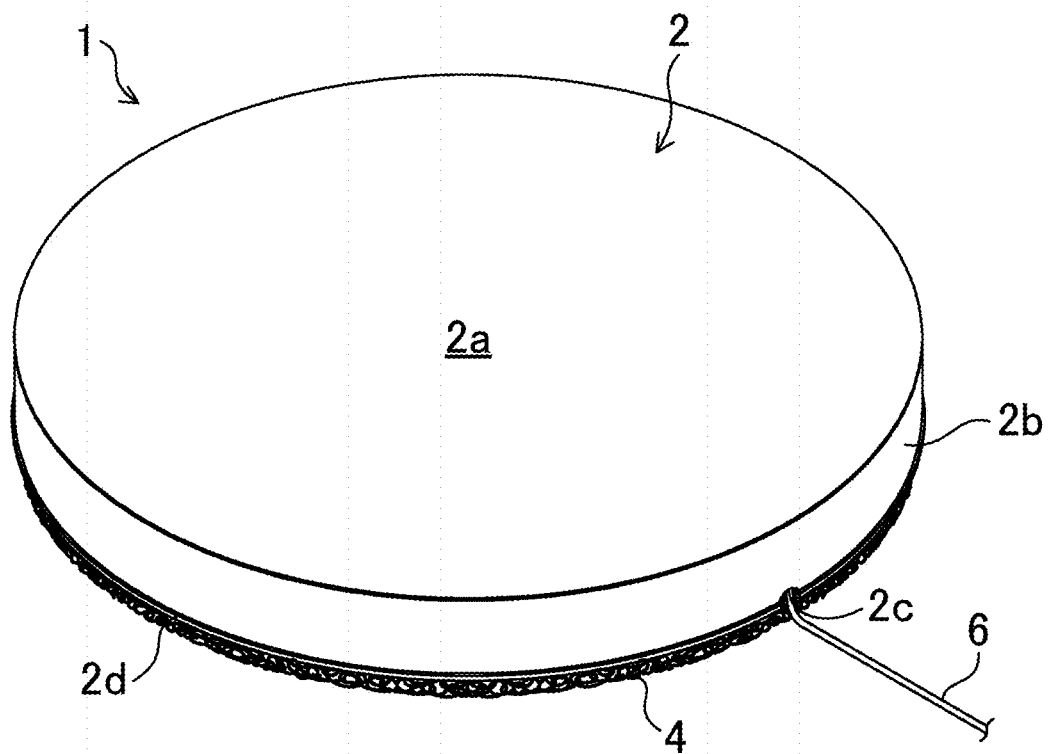
FIG. 1 is a perspective view of an apparatus for bodily sensation of bone vibration according to a first embodiment.

Embodiments will be described with reference to the drawings.

First Embodiment

—Configuration of Apparatus for Bodily Sensation of Bone Vibration—

FIGS. 1 to 4 illustrate an apparatus 1 for bodily sensation of bone vibration according to a first embodiment. The apparatus 1 for bodily sensation of bone vibration includes a metal vibration member 2 having a disc-shaped seat portion 2a configured to contact with a human body, and a side surface portion 2b continuing from the seat portion 2a. In this embodiment, the seat portion 2a is made of a stainless steel sheet having, for example, a diameter of about 600 mm and a thickness of about 2 mm. However, the material and size of the seat portion 2a are not particularly limited. The side surface portion 2b is made of a stainless steel sheet having, for example, a thickness of about 2 mm and a height of about 60 mm. The side surface portion 2b may be fixed to the seat portion 2a by welding or any other means. Alternatively, the side surface portion 2b may be formed integrally with the seat portion 2a. The stainless steel sheet forming the side surface portion 2b is provided with a semicircular cutout 2c having a diameter of, for example, about 20 mm, in order not to interfere with a harness 6 which will be described later. Note that the cutout 2c is not necessarily essential. A rubber member 2d having a U-shaped cross section is fitted on an end of the side surface portion 2b facing a placement plane 3 to protect the end. Note that the rubber member 2d is not necessarily essential. As will be described later in a second embodiment, the vibration member 2 may be made of a thin plate of pure titanium.

Figure 6A:
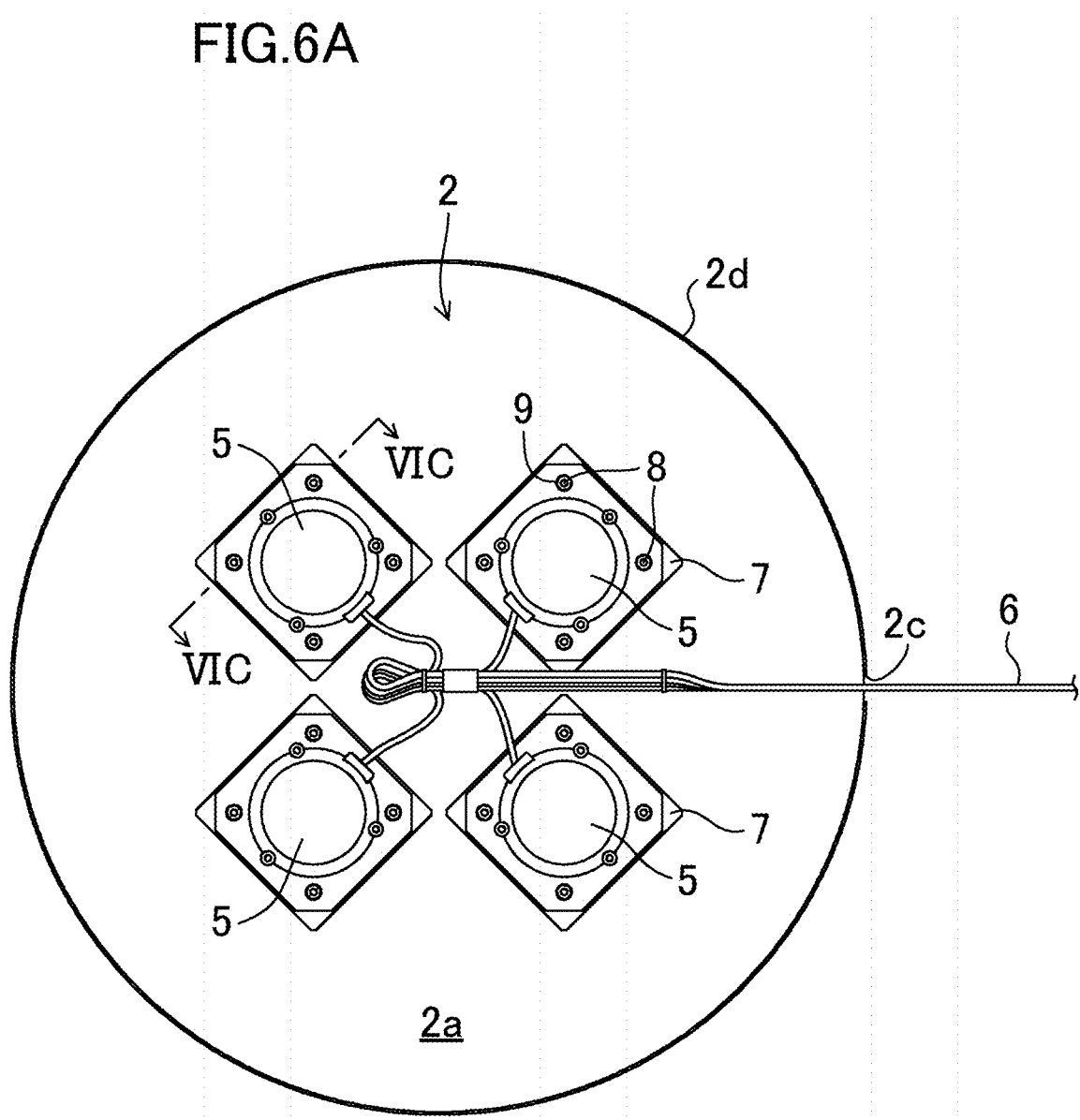
FIG. 6A is a bottom view of the apparatus for bodily sensation of bone vibration according to the first embodiment, with a cushioning material detached from the apparatus.
Figure 6B:
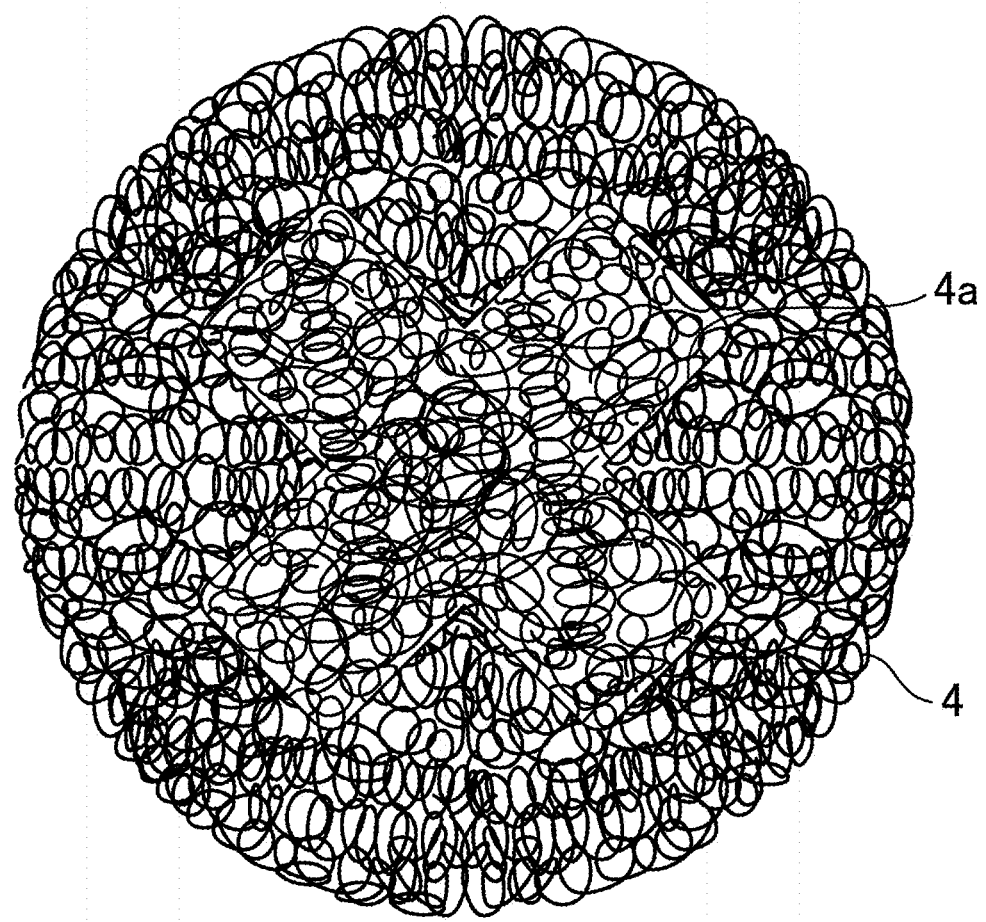
FIG. 6B is a plan view of the cushioning material according to the first embodiment.
Figure 6C:
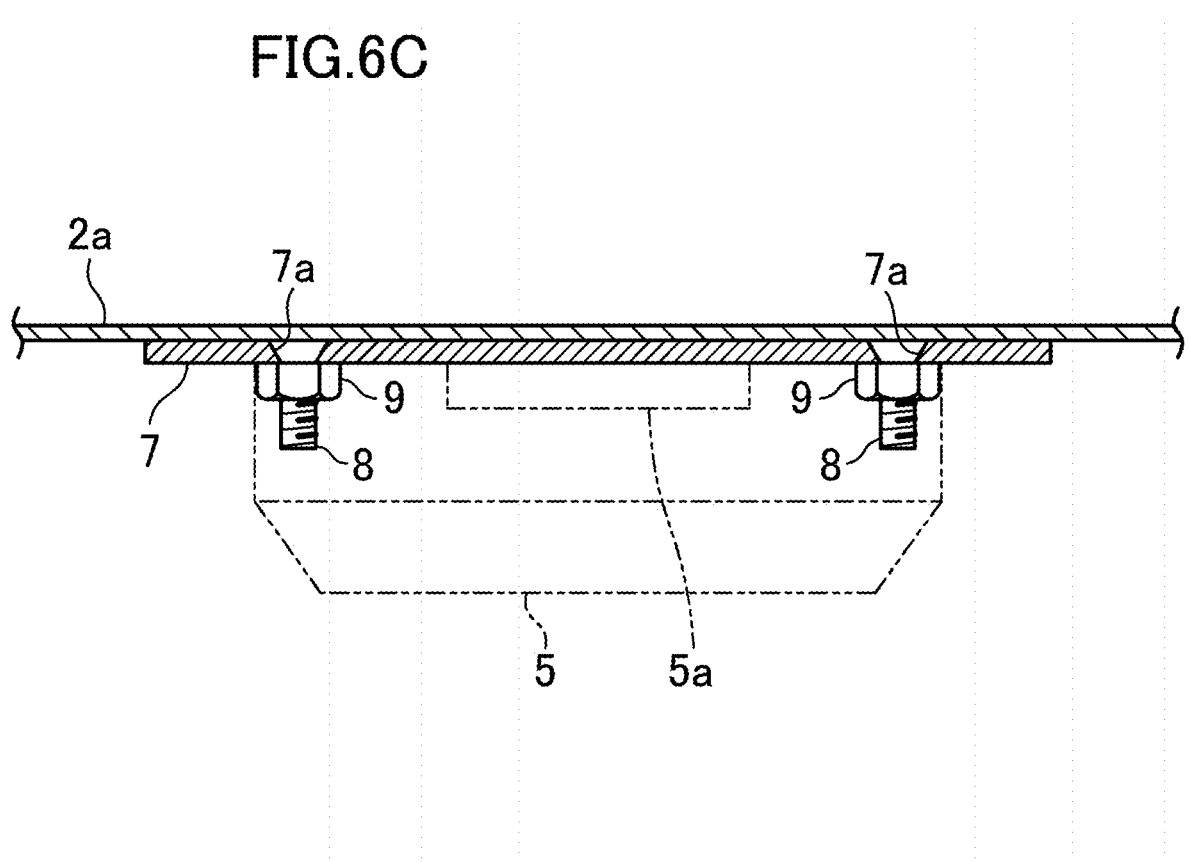
FIG. 6C illustrates, on an enlarged scale, a cross section taken along line VIC-VIC in FIG. 6A.
Figure 7:
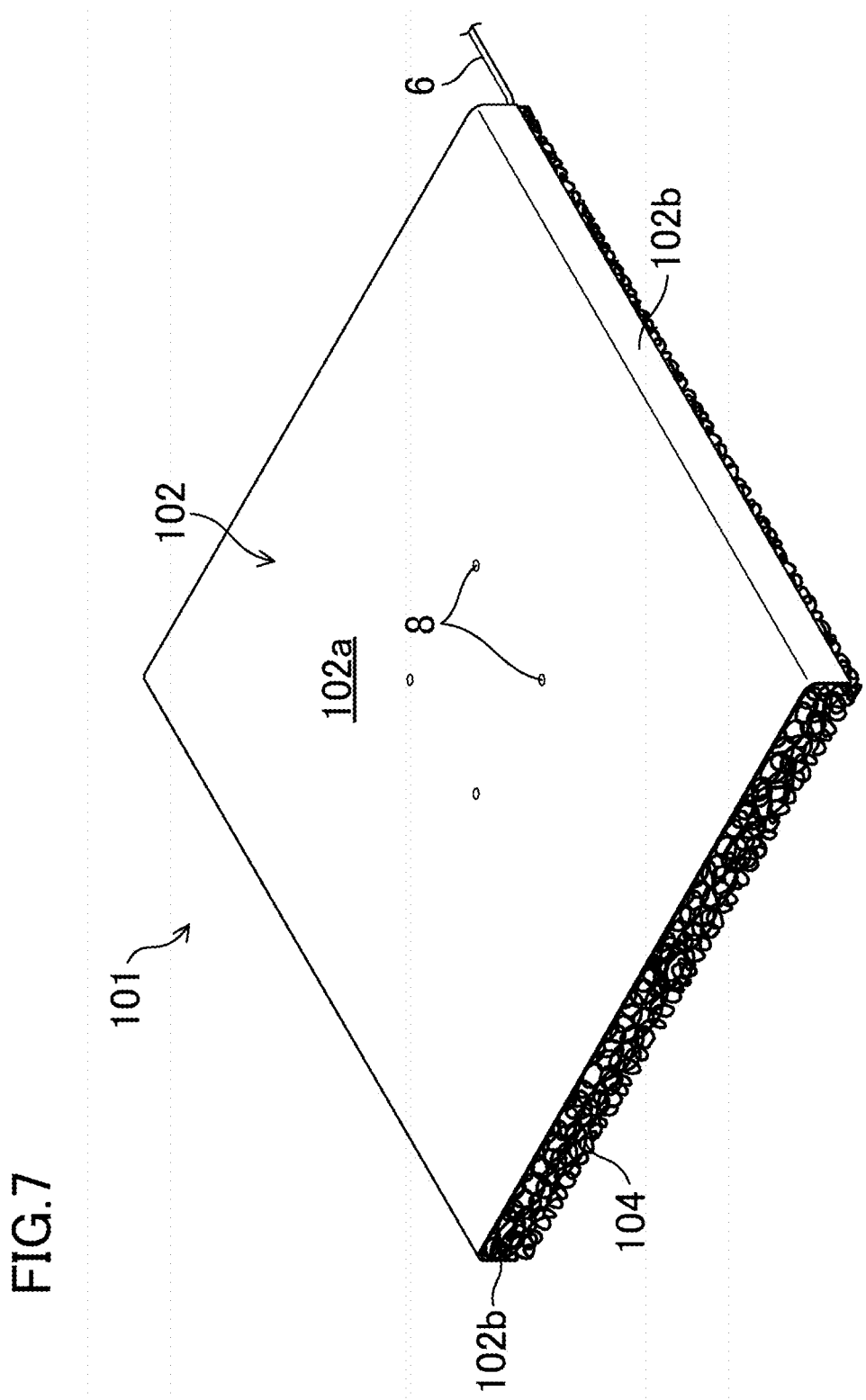
FIG. 7 is a perspective view of an apparatus for bodily sensation of bone vibration according to a second embodiment.
Figure 8:
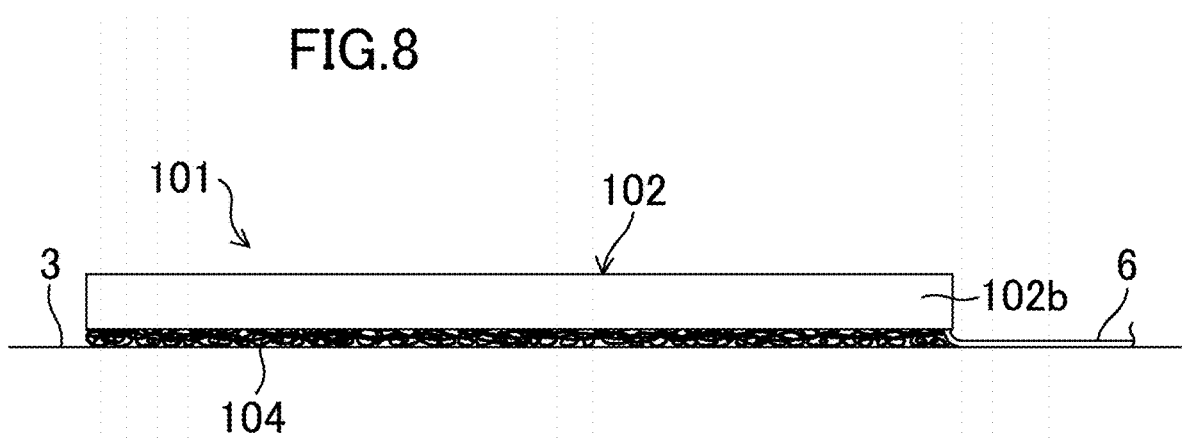
FIG. 8 is a side view of the apparatus for bodily sensation of bone vibration according to the second embodiment.
Figure 9:
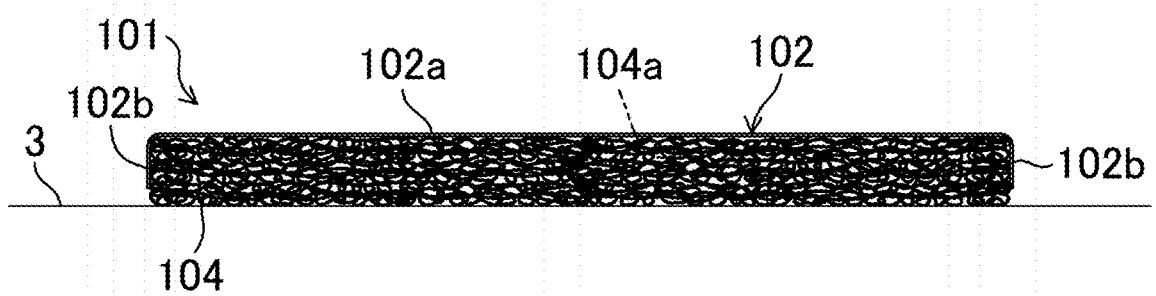
FIG. 9 is a front view of the apparatus for bodily sensation of bone vibration according to the second embodiment.

As illustrated in FIG. 6A, for example, four vibrators 5 are fixed to the back surface of the seat portion 2a. Each of the vibrators 5 is comprised of a high-performance vibration transducer capable of reproducing a vibration within a frequency band of, for example, 16 Hz to 15,000 Hz. As illustrated in FIG. 6C, for example, four drilled holes 7a are formed in a base plate 7 made of a substantially rectangular aluminum plate having a thickness of, for example, about 3 mm, and the vibrators 5 are fastened to the base plate 7 with countersunk screws 8 respectively passing through the drilled holes 7a. The vibrators 5 thus fastened to the base plate 7 are fixed to the back surface of the seat portion 2a with an adhesive or the like. The base plate 7 may be made of any material, and may have any thickness and any shape. Instead of using the base plate 7, the vibrators 5 may be fixed to the seat portion 2a by means of countersunk screws 8, nuts 9, and holes directly drilled in the seat portion 2a. In this manner, a vibration generator 5a of each vibrator 5 is directly coupled to the back surface of the seat portion 2a. Each vibrator 5 has a harness 6 connected to an amplifier 10. The harnesses 6 of the vibrators 5 are tied in a bundle, and the bundle passes through the cutout 2c to be connected to the amplifier 10.

Figure 2:
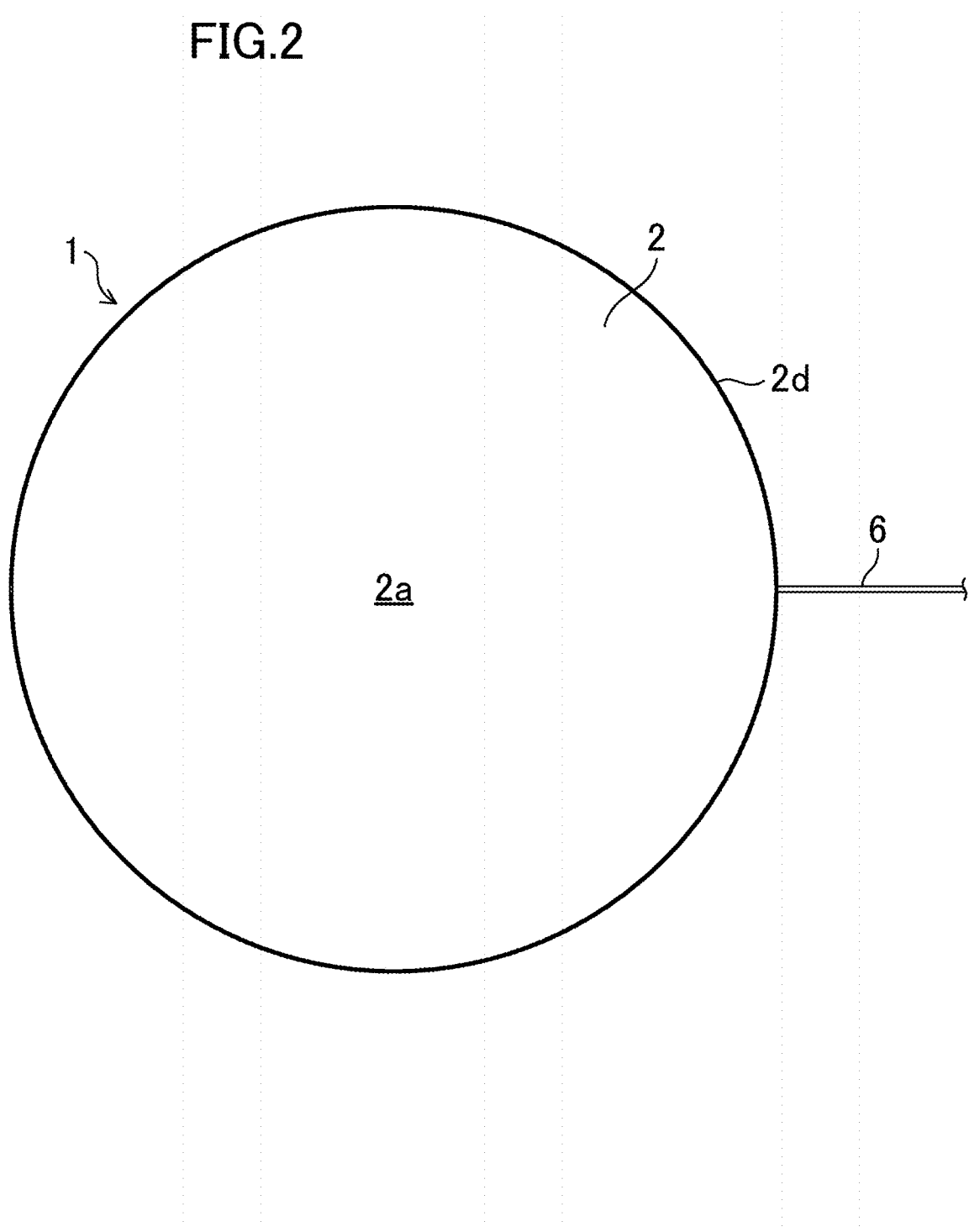
FIG. 2 is a plan view of the apparatus for bodily sensation of bone vibration according to the first embodiment.
Figure 3:
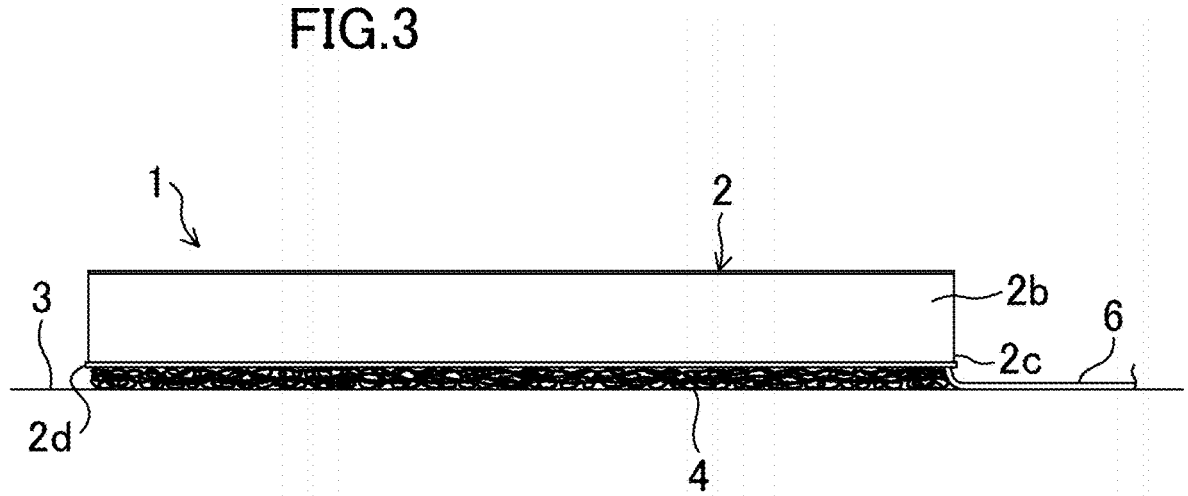
FIG. 3 is a side view of the apparatus for bodily sensation of bone vibration according to the first embodiment.
Figure 4:
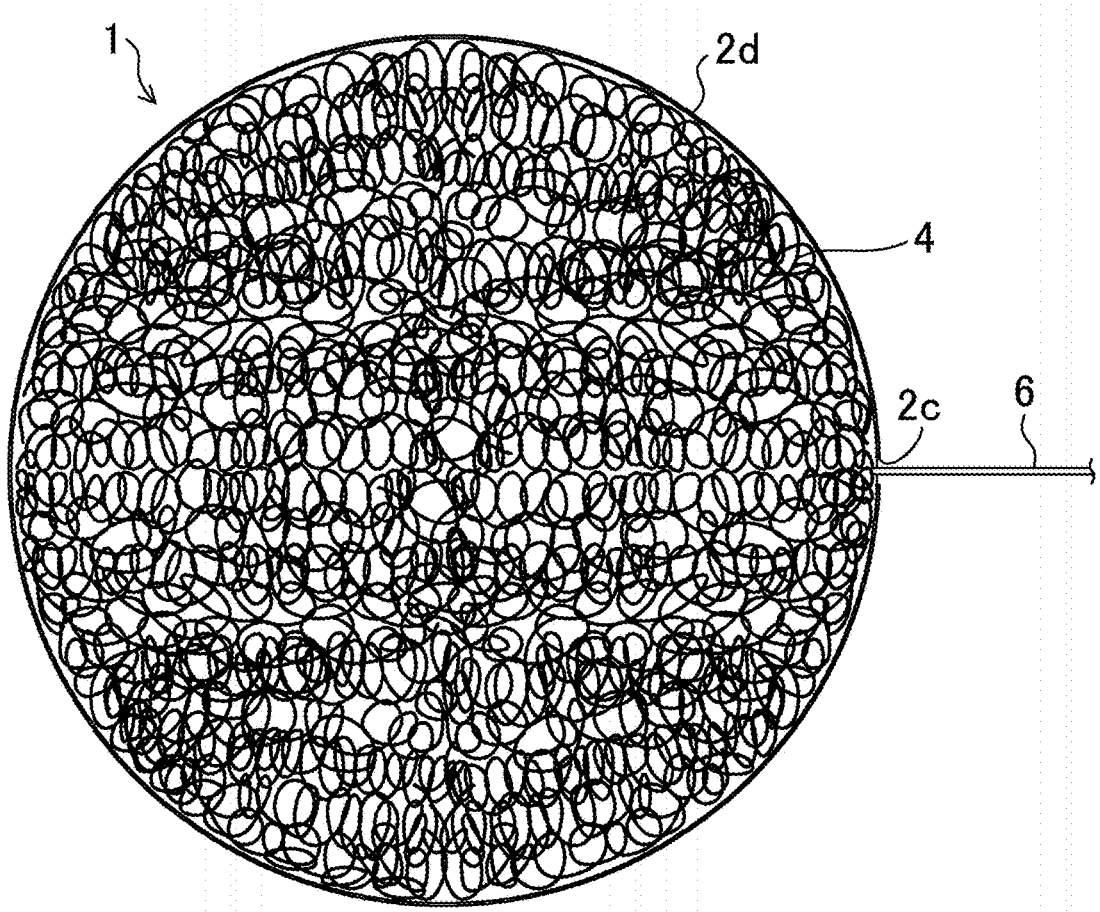
FIG. 4 is a bottom view of the apparatus for bodily sensation of bone vibration according to the first embodiment.

A seat support member 4 is inserted in the vibration member 2 to be disposed on the back surface of the seat portion 2a. The seat support member 4 covers the vibrators 5 and configured to contact with the placement plane 3 such as a floor in a building, so that the seat support member 4 supports the seat portion 2a above and apart from the placement plane 3. The seat support member 4 allows a vibration to be conducted through a part of a human body in contact with the seat portion 2a. As illustrated in FIG. 6B, the seat support member 4 is configured as, for example, a cushioning material comprised of a three dimensional spring structure made of complexly combined fibers of a thermoplastic polyester-based elastomer. The seat support member 4 has, in its surface facing the seat portion 2a, a receiving recess 4a having the shape of a cross and receiving the vibrators 5. As illustrated in FIGS. 1 and 2, an upper portion of the side surface of the seat support member 4 is covered with the side surface portion 2a of the vibration member 2, while the entire periphery of a portion of the seat support member 4 to be adjacent to the placement plane 3 is exposed. The seat support member 4 is inserted in the vibration member 2 while at least a portion of the side surface of the seat support member 4 is compressed by the vibration member 2. For example, if the inside diameter of the vibration member 2 is 596 mm, the seat support member 4 is designed to have an outside diameter slightly larger than 596 mm (e.g., an outside diameter of 600 mm). As a result, the seat support member 4 is fitted in the vibration member 2 while being slightly deformed. Therefore, although not completely fixed by bonding or the like, the seat support member 4 is not detached from the vibration member 2 unless a force is applied by, for example, a pull away from the vibration member 2. The outside shape and the receiving recess 4a of the seat support member 4 may be formed by cutting the three dimensional spring structure, or may be integrally formed using a mold or the like. The height of the seat support member 4 is set to be, for example, 80 mm. The seat support member 4 is high and hard enough to keep the side surface portion 2b from contacting with the placement plane 3 when a user sits on the seat portion 2a.

Figure 5:
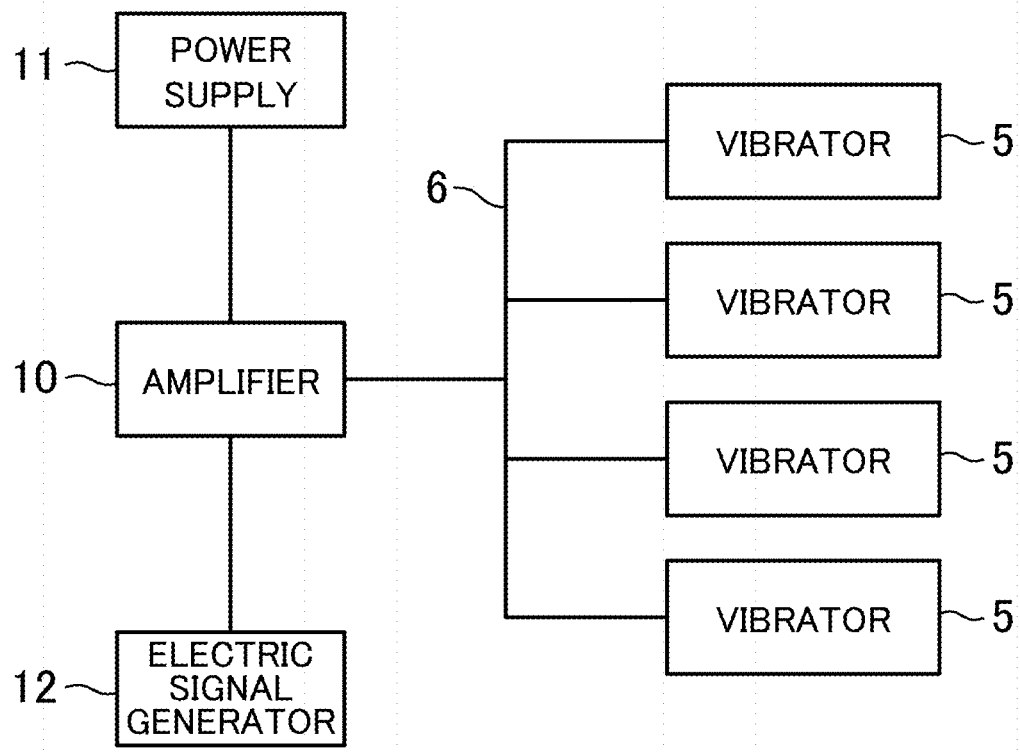
FIG. 5 is a diagram illustrating an overall configuration of the apparatus for bodily sensation of bone vibration according to the first embodiment.

As illustrated in FIG. 5, the amplifier 10 is connected to a power supply 11 of, for example, AC 100 V or AC 120 V, and to an electric signal generator 12. The amplifier 10 serves to amplify an electric signal generated by the electric signal generator 12. The electric signal transmitted from the amplifier 10 is transduced into a mechanical vibration by the vibrators 5.

In this embodiment, for example, the electric signal generator 12 is configured to transmit a specific low frequency corresponding to a compressional wave based on, for example, a linguistic frequency. A fundamental frequency of the "specific low frequency" as used herein is a frequency resulting from conversion of languages in the world, and corresponds to a compressional wave of, for example, 6 Hz to 50 Hz. For example, based on the fact that a combination of a vowel (e.g., a, i, u, e, o) and a consonant (e.g., T, K, M, H, R, N, Y, S, W) generates a sound of a language, the sound is converted to a frequency. The average value of the frequencies of the vowels is approximate to 7.83 Hz that is the value of Schumann Wave, which is the eigenfrequency of the Earth. Further, brain waves are resonant with the Schumann Wave. In view of the foregoing, it has been found that the specific low frequency is conducted more effectively as a vibration that can be sensed in the body than as an audible sound.

For example, the apparatus 1 for bodily sensation of bone vibration of this embodiment generates a vibration which is within a frequency range of about 6 Hz to about 200 Hz and which constitutes a stimulus of continuous pulses. Note that the specific low frequency is not limited to the compressional wave based on the linguistic frequency described above as long as it has a low frequency range of approximately 6 Hz or more and approximately 200 Hz or less.

In addition, the amplifier 10 may be configured to combine the specific low frequency from the electric signal generator 12 with an electric signal from another electric signal generator 12 such as a CD player or the like so as to generate an amplified signal. Alternatively, an electric signal may be transmitted from the electric signal generator 12 using a user's favorite CD or the like which does not include the specific low frequency.

—How to Use Apparatus for Bodily Sensation of Bone Vibration—

It will be described next how to use the apparatus 1 for bodily sensation of bone vibration of this embodiment.

First, the above-described apparatus 1 for bodily sensation of bone vibration is connected to the power supply 11 to cause the electric signal generator 12 to generate an electric signal such as a specific low frequency or the like. The amplifier 10 amplifies the electric signal and transmits the amplified electric signal to the vibrators 5.

In this state, a vibration corresponding to the electric signal and generated by the vibrators 5 is conducted as a bone vibration to the whole body of a user seated on the seat portion 2a via the sacrum of the user. As a result, the vibration as the bone vibration is accurately and effectively conducted from the metal seat portion 2a through the user's sacrum and spinal column to the whole body. Alternatively, the vibration corresponding to the electric signal and generated by the vibrators 5 is conducted as a bone vibration to the whole body of a user standing on the seat portion 2a via the plantar surfaces of the user. As a result, the vibration as the bone vibration is accurately and effectively conducted from the metal seat portion 2a through the user's leg bones and spinal column to the whole body.

This stimulus (vibration) and information contained in the vibration are delivered to the central nervous system via Merkel cells, and exert some influence on the user's brain and consciousness. Note that a honeycomb silicone mat may be placed on the seat portion 2a and the user may sit on the honeycomb silicone mat. The honeycomb silicone mat has a honeycomb structure (expandable structure with multiple hexagonal pores) having a large number of hexagonal pores. In this way, the vibration conducted through the honeycomb silicone mat is sensed on the skin as a continuous alternation of projections and recesses, so that a continuous fine frequency can be conducted to the skin.

When the apparatus 1 for bodily sensation of bone vibration is in operation, the user may practice meditation while looking at an object placed at a predetermined distance from the apparatus 1, for example. Although not illustrated, a suitable example of the object is a piece of obsidian placed on a table made of wood such as Japanese cypress. Alternatively, the object may be a smartphone or the like displaying an image corresponding to the obsidian. Since the three primary colors mixed together at the equal rate result in black, the color of the obsidian, i.e., black, is an all-encompassing color. For example, if the user looks at a piece of obsidian with his/her right and left eyes such that the piece of obsidian becomes integrated with the entire surrounding space, the information about the obsidian is transmitted through the optic chiasma of the user to be processed in the visual area of each level. As a result, the user easily enters the altered state of consciousness. It can be considered that at this time, a flow of Möbius loop (Möbius strip) brings the right and left brains in syntony and makes the information circulate, so that the right and left brains vibrate to resonate. As described above, use of the apparatus 1 for bodily sensation of bone vibration of this embodiment enables a user to effectively practice the so-called digital meditation, which is meditation evolving from Japanese traditional meditation with the help of the latest digital technology. In other words, the apparatus 1 for bodily sensation of bone vibration of this embodiment guides the user to profounder meditation by directly conducting a frequency that has effect on the human body and consciousness. For example, if two or more apparatuses 1 for bodily sensation of bone vibration are arranged in an arc shape around a piece of obsidian and two or more users simultaneously practice the digital meditation, the users can access collective consciousness and easily attain a profounder state. This allows the users to mediate more effectively.

As described earlier, the amplifier 10 may combine the specific low frequency with an electric signal transmitted from a CD player, a smartphone, or the like so as to transmit an amplified signal. In this manner, the user can enjoy healing time with the help of enhanced effect of the specific low frequency, resulting from his/her favorite music carrying the specific low frequency.

This embodiment enables, not a mere physical vibration, but the specific low frequency, to be conducted as a skin vibration or a bone vibration more directly to a human body, i.e., a human brain. As a result, transfiguration and evolution of the psychosomatic health and consciousness are achieved. It can be interpreted that bringing the seat portion 2a into direct contact, or indirect contact via a honeycomb silicone mat or the like, with the skin causes the stimulus (vibration) of the low specific frequency and information contained in the vibration to be delivered to the central nervous system via Merkel cells, and to exert some influence on the brain and consciousness.

As described above, in this embodiment, the configuration in which the side surface portion 2b of the vibration member 2 covers at least a portion of the seat support member 4 improves the external appearance of the apparatus, and makes it difficult for the seat support member 4 to be detached from the vibration member 2. Further, the configuration in which the entire periphery of a portion of the seat support member 4 that is to be adjacent to the placement plane 3 is exposed keeps the side surface portion 2b of the vibration member 2 from contacting with the placement plane 3 when a user sits on the seat portion 2a. As a result, the vibration from the vibrators 5 can be effectively conducted to the body of the user while keeping noise from coming in the vibration.

In addition, in order to reduce conduction of vibrational energy to the placement plane 3 such as a floor, the seat support member 4 supports the seat portion 2a of the metal vibration member 2 above and apart from the placement plane 3 in a state where vibration is difficult to be conducted to the placement plane 3. The seat portion 2a of the vibration member 2 supported in this manner is vibrated by the vibrators 5 so that a human body is directly vibrated through bone conduction or the like. In this manner, an electric signal such as the specific low frequency can be very accurately conducted to the central nervous system and the brain.

In this embodiment, since the seat support member 4 is not bonded to the vibration member 2, but is inserted in a compressed state in the vibration member 2. This configuration makes it easy to assemble and repair the vibrators 5.

Thus, in the apparatus 1 for bodily sensation of bone vibration according to this embodiment, the seat support member 4 supports the seat portion 2a of the metal vibration member 2 above and apart from the placement plane 3 in a state where no vibration is allowed to be conducted to the placement plane 3. The metal seat portion 2a of the vibration member 2 supported in this manner is vibrated by the vibrators 5 so that a human body is directly vibrated through bone conduction. This feature makes it possible to conduct the specific low frequency to a human body as accurately as possible.

Second Embodiment

—Configuration of Apparatus for Bodily Sensation of Bone Vibration—

FIGS. 7 to 13 illustrate an apparatus 101 for bodily sensation of bone vibration according to a second embodiment. The apparatus 101 differs from the apparatus of the first embodiment mainly in the shape of, for example, a vibration member 102 and a seat support member 104, and the number of vibrators 5. Note that in the following embodiments, the same components as those shown in FIGS. 1 to 6C are denoted by the same reference characters, and the detailed explanation thereof will be omitted herein.

The vibration member 102 of this embodiment includes a seat portion 102a having the shape of, for example, a rectangular plate, and side surface portions 102b continuing with two opposite sides of the seat portion 102a and forming a bend angle of about 90° with the two opposite sides. For example, the seat portion 102a of the vibration member 102 is in the shape of a square having a side of 600 mm. Note that, the side surface portion 102b may be configured to continuously extend along the entire periphery of the seat portion 102a, as in the first embodiment. As the vibration member 102 of this embodiment, for example, a plate member of pure titanium subjected to crystal decoration processing with an oxide film of titanium oxide. The vibration member 102 is formed simply by bending this plate member. Thus, the vibration member 102 is easy to produce, has very attractive external appearance, and provides photo-antimicrobial effect and the like which increase the commercial value.

Figure 11:
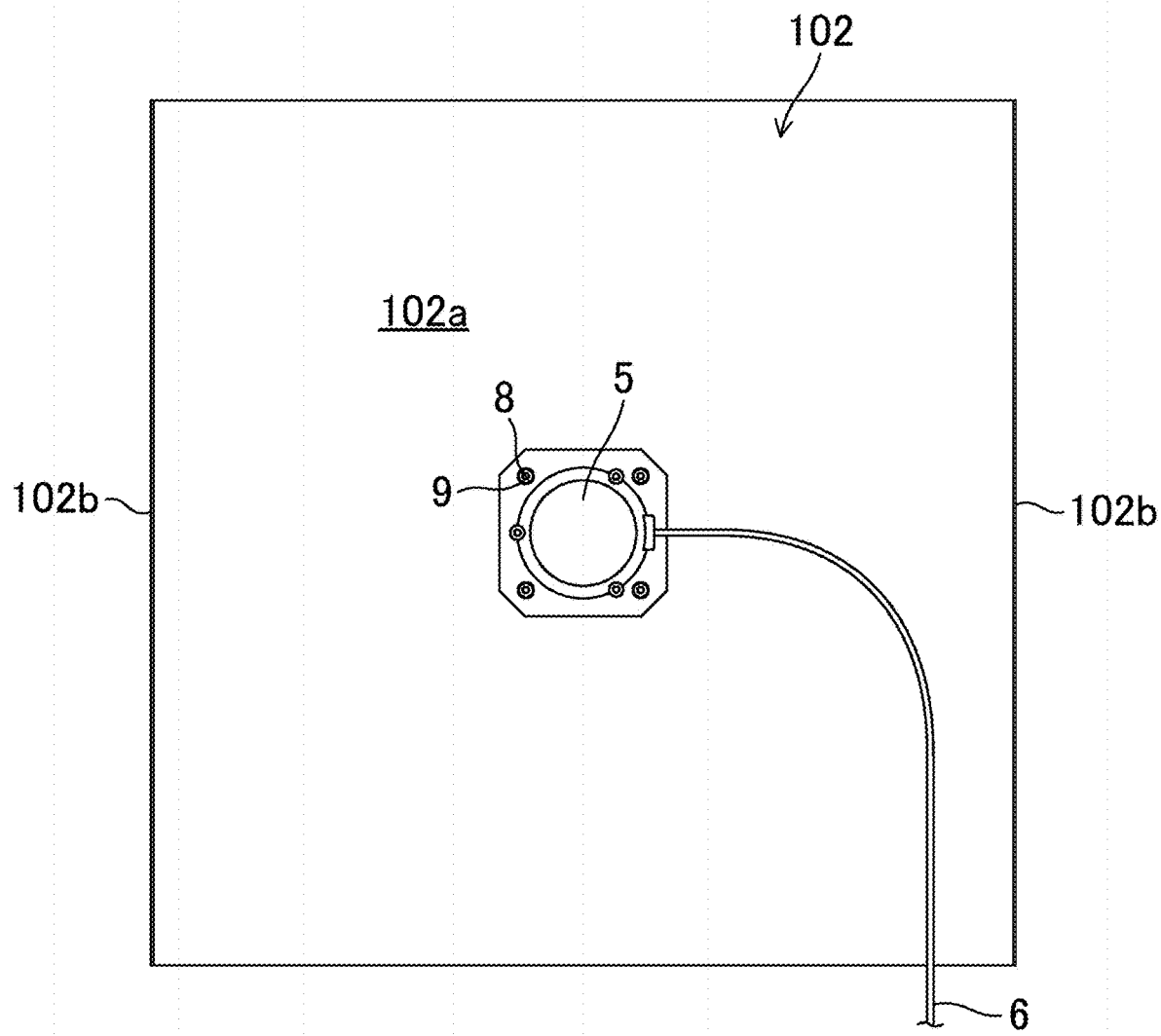
FIG. 11 is a bottom view of the apparatus for bodily sensation of bone vibration according to the second embodiment, with a cushioning material detached from the apparatus.

In this embodiment, as illustrated in FIG. 11, for example, one vibrator 5 is fixed to a central area of the back surface of the rectangular seat portion 102a in the same manner as in the first embodiment. Alternatively, two vibrators 5 may be fixed to a central area of the seat portion 102a. For example, the vibrator 5 is fixed to the back surface of the seat portion 102a using countersunk screws 8 passing through holes drilled in the seat portion 102a and nuts 9. Note that the number of the vibrators 5 is not particularly limited, and the vibrators 5 may be fixed to any position in any manner. The vibrator 5 may be fixed in the same manner as in the first embodiment.

The seat support member 104 of this embodiment is in a rectangular shape conforming to the shape of the vibration member 102, and has an outside shape as large as, or slightly larger than, the outside shape of the seat portion 102a. Similarly to the first embodiment, the seat support member 104 of this embodiment has a rectangular receiving recess 104a provided at a position corresponding to the vibrator 5. For example, if the height of the side surface portions 102b is about 40 mm, the seat support member 104 having a height of about 50 mm is used. The seat support member 104 is high and hard enough to keep the side surface portions 102b from contacting with the placement plane 3 when a user sits on the seat portion 102a.

Figure 10:
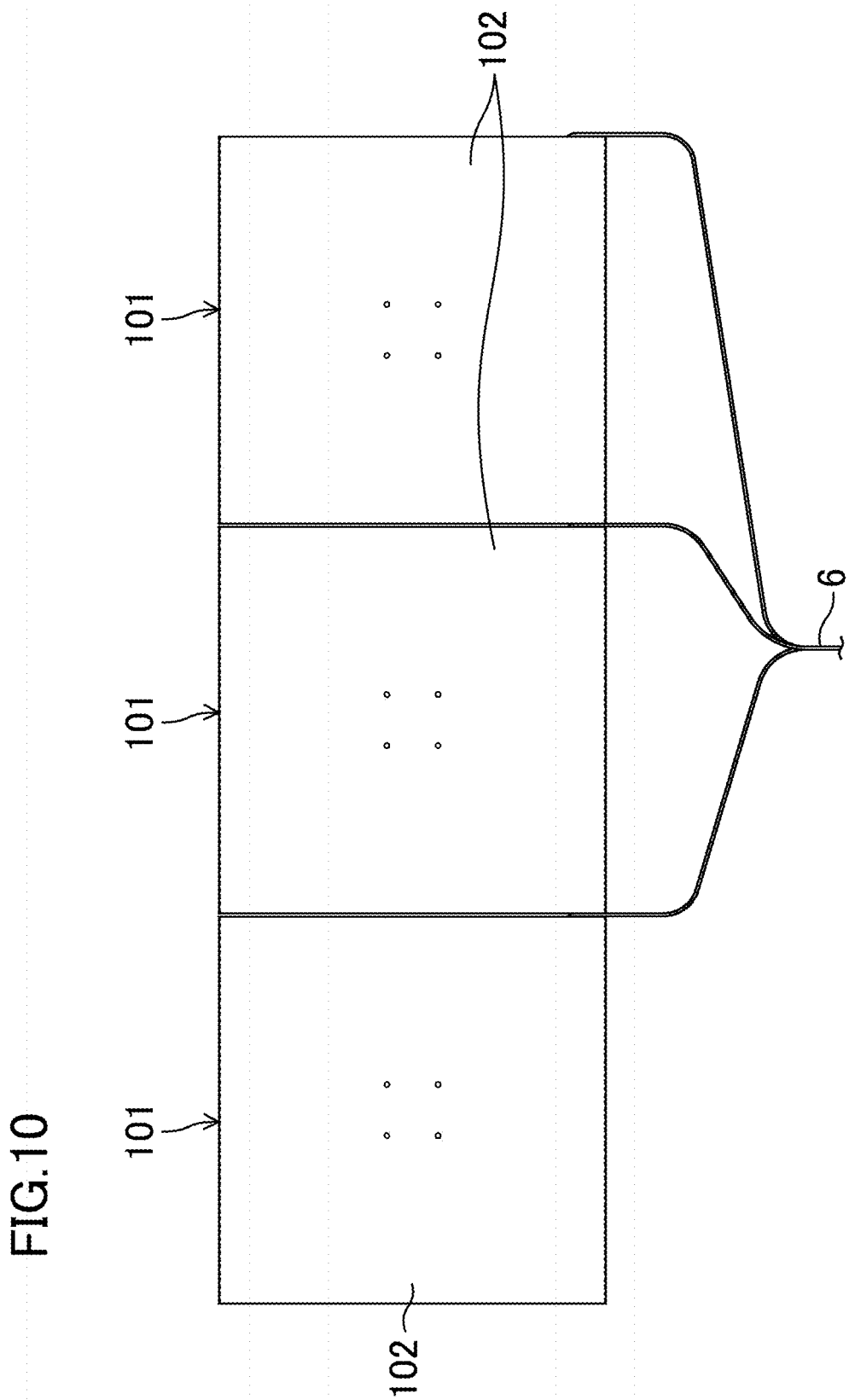
FIG. 10 is a plan view illustrating a state in which three apparatuses for bodily sensation of bone vibration according to the second embodiment are arranged adjacent to each other.

As illustrated in FIGS. 10 and 13, for example, three apparatuses 101 for bodily sensation of bone vibration of this embodiment can be arranged in a straight line to form a bed.

Figure 12:
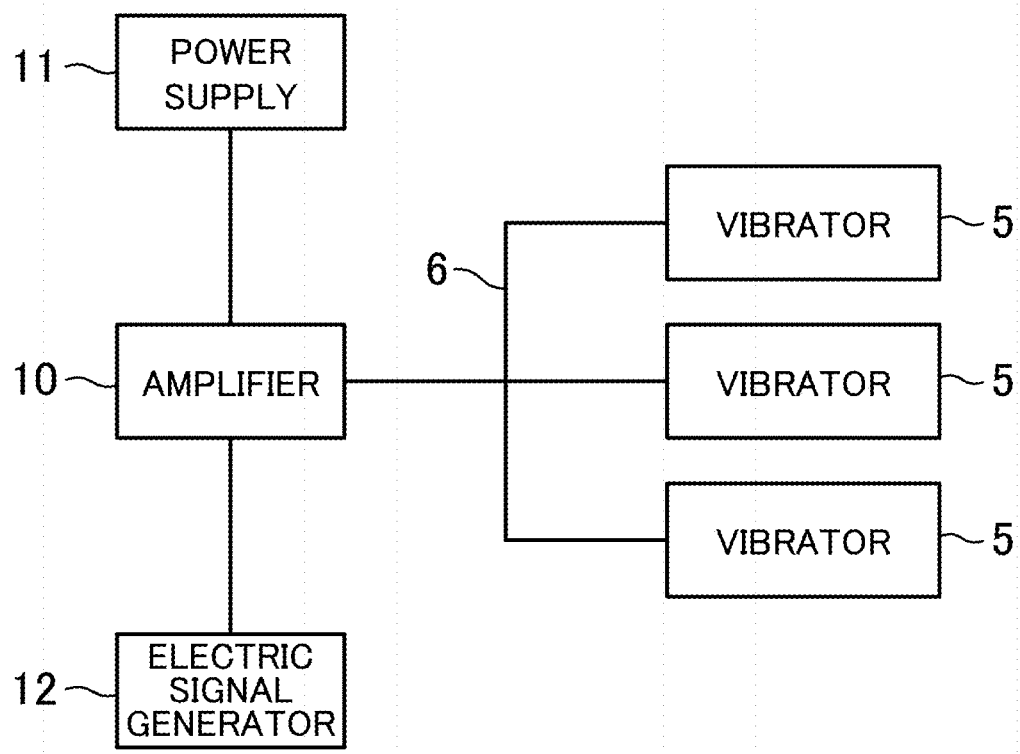
FIG. 12 is a diagram illustrating an overall configuration of the apparatus for bodily sensation of bone vibration according to the second embodiment.

As illustrated in FIG. 12, an amplifier 10 transmits an electric signal containing the specific low frequency, for example, to each of the vibrators 5 in the same manner as in the first embodiment.

—How to Use Apparatus for Bodily Sensation of Bone Vibration—

It will be described next how to use the apparatus 101 for bodily sensation of bone vibration of this embodiment.

First, as illustrated in FIGS. 10 and 13, three apparatuses 101 for bodily sensation of bone vibration are arranged such that the sides of the vibration members 102 where the side surface portions 102b are not provided face each other. As illustrated in FIG. 12, devices are connected to the apparatuses 101 and actuated, so that an electric signal is transmitted to the vibrator 5 of each of the apparatuses 101. The electric signal is transmitted in the same manner as in the first embodiment. As illustrated in FIG. 13 as an example, data stored in a PC 114 including a CPU, a hard disk, a communication device, a storage device, and various programs may be transferred to a smartphone 112, and the data may be transmitted from the smartphone 112 to the amplifier 10.

As can be seen, a user 115 can lie over two or more apparatuses 101 for bodily sensation of bone vibration arranged in a straight line. Thus, a vibration can be conducted through the whole body of the user. For example, the vibration can be conducted via Merkel cells that sense a pressure of touch on a human skin. Thus, the vibration can be conducted while the user is in a more relaxed posture.

As illustrated in FIG. 13 as an example, three apparatuses 101 for bodily sensation of bone vibration may be arranged so that the seat portions 102a are substantially continuous with each other, and one honeycomb silicone mat 113 having an expandable structure with multiple hexagonal pores may be placed over the seat portions 102a. The vibration may be conducted as a bone vibration to the whole body of the user 115 lying on the honeycomb silicone mat 113.

Since the apparatuses 101 for bodily sensation of bone vibration are arranged so that the sides of the vibration members 102 without the side surface portions 102b face each other, adjacent ones of the vibration members 102 are prevented from contacting with each other, and each apparatus 101 effectively conducts a vibration to the user's body.

As a result, the apparatus 101 for bodily sensation of bone vibration of this embodiment can also conduct the specific low frequency to a human body as accurately as possible.

Instead of arranging the three apparatus 101 for bodily sensation of bone vibration of this embodiment closely adjacent to each other, the apparatuses 101 may be arranged at intervals so that a user can sits on the seat portion 102a of each apparatus 101 for bodily sensation of bone vibration. Alternatively, one apparatus 101 for bodily sensation of bone vibration may be used alone in the same manner as in the first embodiment.

Other Embodiments

The above embodiments may be configured as follows.

In the above embodiments, the seat support member 4, 104 is configured as a cushioning material comprised of a three dimensional spring structure made of complexly combined fibers of a thermoplastic polyester-based elastomer. However, this is merely a non-limiting example. The seat support member 4, 104 may be comprised of a three dimensional spring structure including a reinforcing material integrally embedded therein, or having an increased density in a portion close to the placement plane. Alternatively, another material having appropriate hardness and elasticity, such as urethane, may be used as the seat support member 4, 104 to support the seat portion 2a, 102a above and apart from the placement plane 3 so that conduction of vibrational energy to the placement plane 3 is reduced when the apparatus 1, 101 is placed on the placement plane 3.

In the above embodiments, the amplifier 10 is provided outside the vibration member 2, 102. However, as illustrated in FIG. 13, the amplifier 10 may be incorporated in the vibration member 2, 102. This configuration eliminates the need to place the amplifier 10 separate from the apparatus for bodily sensation of bone vibration.

The foregoing embodiments are merely preferable examples in nature, and are not intended to limit the scope, applications, or use of the present disclosure.

What is claimed is:
1. An apparatus for bodily sensation of bone vibration, the apparatus comprising:
an electric signal generator configured to generate an electric signal;
an amplifier configured to amplify the electric signal from the electric signal generator;
a vibrator configured to transduce the amplified electric signal transmitted from the amplifier into a mechanical vibration;
a metal vibration member directly coupled to a vibration generator of the vibrator, the vibration member having a seat portion configured to contact with a human body and a side surface portion continuing with the seat portion; and
a seat support member provided on a back surface of the seat portion, covering the vibrator, and configured to be placed on a placement plane and to support the seat portion above and apart from the placement plane so as to keep vibrational energy from being conducted to the placement plane, wherein
at least a portion of a side surface of the seat support member is covered with the side surface portion of the vibration member, and the apparatus for bodily sensation of bone vibration is configured to conduct the vibration as a bone vibration via a part of the human body, the part being in contact with the seat portion.

2. The apparatus of claim 1, wherein
the vibration member is made of a metal sheet or plate,
the seat support member is comprised of a cushioning material, and has a receiving recess for receiving the vibrator, and
at least a portion of a side surface of the cushioning material is covered with the side surface portion of the vibration member while an entire periphery of a portion the cushioning material to be adjacent to the placement plane is exposed.

3. The apparatus of claim 2, wherein
the cushioning material is inserted in the vibration member while at least the portion of the side surface of the cushioning material is compressed by the vibration member.

4. The apparatus of claim 1, wherein
the electric signal generator is configured to transmit a specific low frequency corresponding to a compressional wave.

5. The apparatus of claim 4, wherein
the electric signal generator is configured to transmit the specific low frequency corresponding to the compressional wave based on a linguistic frequency.

6. The apparatus of claim 1, wherein
the apparatus for bodily sensation of bone vibration includes a plurality of apparatuses for bodily sensation of bone vibration arranged adjacent to each other, the seat portion of the vibration member of each of the plurality of apparatuses for bodily sensation of bone vibration has a rectangular shape, the electric signal is transmitted to the vibrator of each of the plurality of apparatuses for bodily sensation of bone vibration.

7. The apparatus of claim 6, wherein
the vibration member is made of a metal sheet or plate,
the seat support member is comprised of a cushioning material, and has a receiving recess for receiving the vibrator, and
at least a portion of a side surface of the cushioning material is covered with the side surface portion of the vibration member while an entire periphery of a portion the cushioning material to be adjacent to the placement plane is exposed.

8. The apparatus of claim 7, wherein
the amplifiers of the plurality of apparatus for bodily sensation of bone vibration are configured as a single amplifier shared by the plurality of apparatus and is incorporated in any one of the apparatuses for bodily sensation of bone vibration.

9. The apparatus of claim 6, wherein
the vibration member is made of a plate member of pure titanium subjected to crystal decoration processing with an oxide film of titanium oxide.

10. The apparatus of claim 6, further comprising one honeycomb silicon mat having an expandable structure with multiple hexagonal pores is placed over the seat portions of the plurality of apparatuses for bodily sensation of bone vibration arranged adjacent to each other, and
the vibration is conducted as the bone vibration to the whole body of the user lying on the honeycomb silicon mat.

11. An apparatus for bodily sensation of bone vibration, the apparatus comprising:
an electric signal generator configured to generate an electric signal;
an amplifier configured to amplify the electric signal from the electric signal generator;
a vibrator configured to transduce the amplified electric signal transmitted from the amplifier into a mechanical vibration;
a metal vibration member directly coupled to a vibration generator of the vibrator, the vibration member having a seat portion configured to contact with a human body and a side surface portion continuing with the seat portion; and
a seat support member provided on a back surface of the seat portion, covering the vibrator, and configured to be placed on a placement plane and to support the seat portion above and apart from the placement plane so as to keep vibrational energy from being conducted to the placement plane, wherein
the vibration member is made of a metal sheet or plate,
the seat support member is comprised of a cushioning material, and has a receiving recess for receiving the vibrator,
at least a portion of a side surface of the cushioning material is covered with the side surface portion of the vibration member while an entire periphery of a portion the cushioning material to be adjacent to the placement plane is exposed, and
the apparatus for bodily sensation of bone vibration is configured to conduct the vibration as a bone vibration via a part of the human body, the part being in contact with the seat portion.

* * * * *